United States Patent

Guittard et al.

Patent Number: 5,358,721
Date of Patent: Oct. 25, 1994

[54] ANTIVIRAL THERAPY

[75] Inventors: George V. Guittard, Cupertino; Patrick S. L. Wong, Palo Alto; Anthony L. Kuczynski, Mountain View; David J. Kidney, Palo Alto, all of Calif.

[73] Assignee: Alza Corporation, Palo Alto, Calif.

[21] Appl. No.: 985,989

[22] Filed: Dec. 4, 1992

[51] Int. Cl.⁵ .................................................. A61K 9/24
[52] U.S. Cl. ..................................... 424/473; 424/468; 604/891.1
[58] Field of Search ........................ 424/473, 468; 604/891.1

[56] References Cited

U.S. PATENT DOCUMENTS

| 2,799,241 | 7/1957 | Wurster | 118/24 |
|---|---|---|---|
| 3,845,770 | 11/1974 | Theeuwes et al. | 128/260 |
| 3,854,480 | 12/1974 | Zaffaroni | 128/260 |
| 3,916,899 | 11/1975 | Theeuwes et al. | 128/260 |
| 4,063,064 | 12/1977 | Saunders et al. | 219/121 L |
| 4,088,864 | 5/1978 | Theeuwes et al. | 219/121 LM |
| 4,160,020 | 7/1979 | Ayer et al. | 424/15 |
| 4,200,098 | 4/1980 | Ayer et al. | 128/260 |
| 4,285,987 | 8/1981 | Ayer et al. | 427/3 |
| 4,327,725 | 5/1982 | Cortese et al. | 128/260 |
| 4,612,008 | 9/1986 | Wong et al. | 604/892 |
| 4,765,989 | 8/1988 | Wong et al. | 424/473 |
| 4,783,337 | 11/1988 | Wong et al. | 424/468 |
| 4,950,486 | 8/1990 | Ayer et al. | 424/473 |

Primary Examiner—Thurman K. Page
Assistant Examiner—Jyothsna Venkat
Attorney, Agent, or Firm—Paul L. Sabatine; Alisa A. Harbin; Richard T. Ito

[57] ABSTRACT

A dosage form is disclosed for administering an antiviral drug to a patient in need of antiviral therapy.

15 Claims, 1 Drawing Sheet

ANTIVIRAL THERAPY

FIELD OF THE INVENTION

This invention pertains to a pharmaceutical antiviral composition and to a dosage form for dispensing the pharmaceutical composition. The invention relates further to a method of administering an antiviral drug to a patient infected with a virus to minimize the virus infection in the patient.

BACKGROUND OF THE INVENTION

A considerable and continuous need exists for (1) a pharmaceutical composition comprising an antiviral drug, for (2) a controlled release dosage form comprising the pharmaceutical composition, and for (3) a method for treating a virus infection by administering an antiviral drug composition to a patient in need of antiviral therapy.

The need exists for dispensing means including a pharmaceutical composition and for a dosage form because during the past years various antiviral chemotherapeutic drugs were synthesized for treating virus infections, while concomitantly the dispensing art did not provide a pharmaceutical composition and dosage form for dispensing the antiviral drug to a patient in need of antiviral therapy. For example, the antiviral compound 9-(2-hydroxy-ethoxymethyl)-guanine, also known as acyclovir, possesses potent antiviral activity, is available for treating herpes virus, yet acceptable means are not available for dispensing this drug to a patient in need of it. This antiviral drug and other antiviral drugs exhibit poor aqueous solubility and thus do not lend themselves for formulating into a pharmaceutical composition for subsequent dispensing from a dosage form. That is, generally this physical-chemical property severely limits antiviral drug formulation fluid during operation of the dosage form.

In the light of the above presentation, it will be appreciated by those versed in the antiviral art, to which this invention pertains, that a demand exists for a pharmaceutical composition and for a dosage form that can deliver a difficult to deliver antiviral drug at a known and controlled rate to a patient in need of antiviral therapy. The demand exists for an oral composition and dosage form that can deliver an antiviral drug at a controlled rate and at a constant dose per unit time. The demand exists for dispensing means for gastrointestinal delivery of antiviral drugs for obtaining antivirus hemodynamic effects that are free of fluid wash-out, and substantially independent of the variable environment of the gastrointestinal tract. It will be appreciated further by those versed in the antiviral art that if a novel and nonobvious antiviral composition and dosage form are provided, they would represent an advancement and valuable improvement in the antiviral therapeutic art.

OBJECTS OF THE INVENTIONS

Accordingly, in view of the above presentation, it is an immediate object of this invention to provide both a novel pharmaceutical composition comprising an antiviral drug and a novel dosage form comprising the antiviral composition, which manufactures overcome the shortcoming known to the prior art.

Another object of the present invention is to provide a pharmaceutical composition comprising an antiviral drug that can be dispensed from a dosage form in an aqueous biological environment of use.

Another object of the present invention is to provide a dosage form comprising an antiviral drug that can be delivered by the dosage form in an aqueous environment substantially-free of environmental aqueous influence at a controlled rate to provide antiviral therapy.

Another object of the present invention is to provide a dosage form manufactured as an osmotic device that substantially reduces and/or eliminates the unwanted influences of the gastrointestinal tract, and which osmotic dosage form still provides controlled administration of the antivirus drug over time.

Another object of the present invention is to provide a pharmaceutical composition comprising an antiviral drug and a polymeric carrier for the antiviral drug, which when combined, will translocate throughout the gastrointestinal tract and therapy provide antiviral drug to the cellular wall of the gastrointestinal tract for the intended therapy.

Another object of the present invention is to provide a delivery means for dispensing an antiviral drug for effective reducing of a virus disease resulting from a virus infection.

Another object of the invention is to provide a pharmaceutical composition and a controlled-release dosage form, which manufactures are useful for the treatment of vital infections.

Another object of the present invention pertains to a method of administering an antiviral drug to a patient infected with a herpes virus including virus infections selected from the group consisting of ovolabial herpes, cutaneous herpes, genital herpes, herpetic proctitis, varicella-zoster herpes and wart herpes.

Another object of the present invention pertains to a method of administering an antiviral drug through osmotic delivery to a patient infected with a vital disease caused by a virus that replicates by reverse transcription to minimize the effects of the virus infection.

Another object of the invention is to provide a method of treating a human having acquired immunodeficiency syndrome wherein the method comprises administering osmotically an effective dose of a vital inhibiting drug to lessen the acquired immunodeficiency syndrome.

Another object of this invention is to provide a hydro-activated osmotic dosage form comprising a compartment containing a member selected from the group consisting of an antiviral drug, its nontoxic salts, racemic mixtures, enantiomer, esters and salts of esters that are administered in a clinically effective dose for treating vital infections.

Another object of the invention is to provide an osmotic dosage form adapted and sized for orally administering an antiviral drug, which dosage from comprises a first antiviral composition and a second displacement composition that act in harmony as a unit dosage form wherein the dosage form is characterized by delivering the poorly soluble antiviral drug essentially free of retention by the ingredients comprising the antiviral composition.

Another object of the invention is to administer two different antiviral drugs from an osmotic dosage form for antiviral therapy.

Other objects, features and advantages of this invention will be more apparent to those versed in the dispensing and antivirus arts from the following detailed specification taken in conjunction with the drawings and the accompanying claims.

BRIEF DESCRIPTION OF THE DRAWING

In the drawing figures, which are not drawn to scale, but which drawing figures are set forth to illustrate various embodiments of the invention, the drawing figures are as follows:

Drawing

Drawing

Drawing FIG. 4 depicts the drawing figure comprising a surface having a multiplicity of release-rate governing pores for administering an antiviral drug at a controlled rate per unit time over time.

Figure 1:
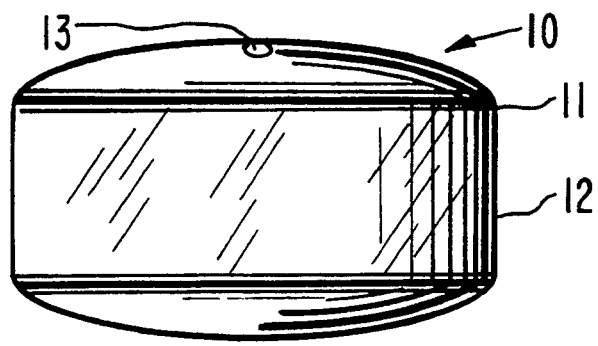
FIG. 1 is a view of a dosage form provided by the invention and manufactured as an osmotic dosage form sized and shaped for orally administering an antiviral drug to a patient in need of antiviral therapy.

In the drawing figures and in the specification, like parts and like ingredients in related drawing figures are identified by like numbers. The terms appearing earlier in the specification, and in the description of the drawing figures, as well as various embodiments thereof, are further described elsewhere in the disclosure.

DETAILED DESCRIPTION OF THE DRAWING FIGURES

Turning now to the drawing figures in detail, which drawing figures are an example of the dosage form provided by the invention, which dosage form contains an antiviral pharmaceutical composition, and which examples are not to be considered as limiting the invention, one example of the dosage form is illustrated in accompanying drawing FIGS. 1 to 4.

In drawing FIG. 1, a dosage form 10 is seen designated by the numeral 10. Dosage form 10 comprises a body member 11 comprising wall 12. Wall 12 surrounds and defines an internal compartment, not seen in drawing FIG. 1. Dosage form 10 comprises at least one exit passageway 13 for connecting the interior of dosage form 10 with the exterior environment of use.

Figure 2:
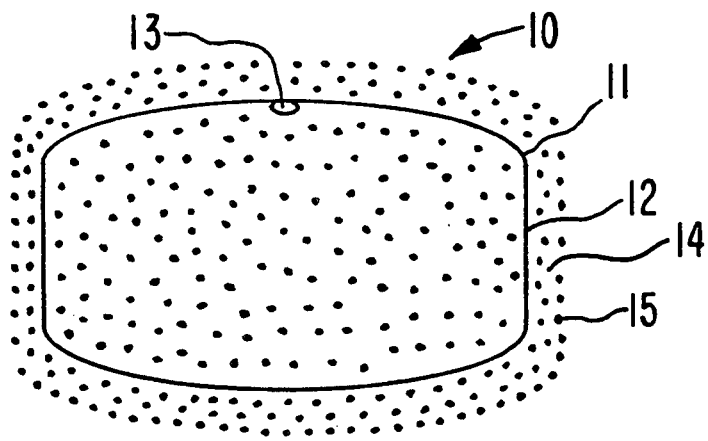
FIG. 2 is a view of a dosage form provided by the invention which dosage form comprises an exterior dose of an antiviral drug for effecting an instant dose of an antiviral drug to a warm-blooded animal.

Dosage form 10, as seen in drawing FIG. 2, comprises body 11, wall 12, exit means 13 and an exterior lamina 14. Exterior lamina 14 comprises a dosage unit amount of an antiviral drug 15 for providing an immediate dose of antiviral drug 15 through the oral passageway into the gastrointestinal tract of a warm-blooded animal. The immediate dose is a first dose of drug 15 from the exterior of dosage form 10. A second dose of drug 15 is provided from an internal compartment, not seen in drawing FIG. 2, from the dosage form 10. The manufacture seen in drawing FIG. 2, comprises two doses of drug 15, and in this manufacture it is a two dose dosage form. Exterior lamina 14 comprises 0.01 nanogram to 1.5 grams of a pharmaceutically acceptable carrier for antiviral drug 15. The pharmaceutically acceptable carrier is a means for coating and carrying drug 15 on the exterior surface of wall 12. In the fluid environment of the gastrointestinal tract, the pharmaceutical carrier releases drug 15, thereby providing an immediate dose of antiviral drug. The carrier releases the immediate dose in from 30 seconds up to one hour, and in a presently preferred immediate dose time from 1.5 minutes up to 30 minutes. The pharmaceutically acceptable carrier for forming immediate release lamina 14 comprises 100 ng to 150 mg a member selected from the group consisting of a hydrophilic polymer, hydroxymethylcellulose, hydroxyethylcellulose, hydroxypropylcellulose, hydroxypropylmethylcellulose, hydroxyalkylcellulose, and hydroxypropylethylcellulose.

Figure 3:
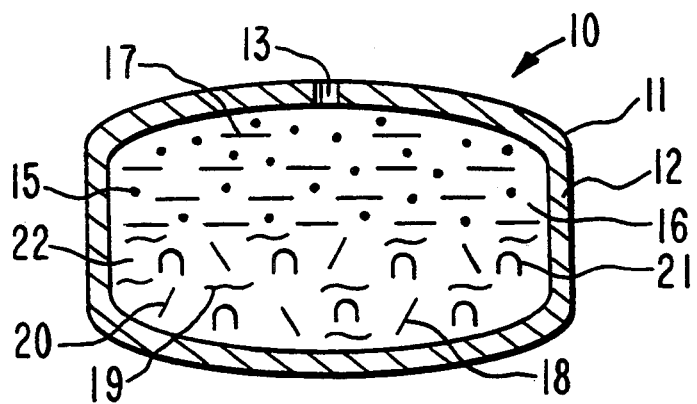
FIG. 3 is an opened view of the dosage form of drawing FIG. 1 for illustrating the internal structure and the internal ingredients of the dosage form; and Drawing
Figure 4:
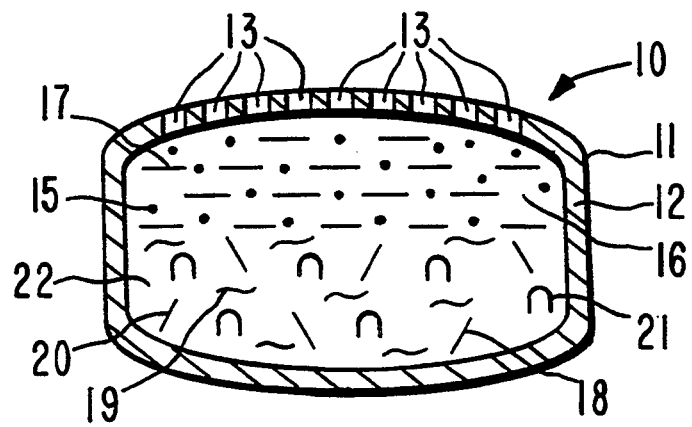
FIG. 4 is a view of the dosage form of FIG. 1, which drawing

Dosage form 10, as seen in drawing FIG. 3, illustrates another embodiment provided by the invention. In drawing FIG. 3, dosage form 10 is seen in opened view comprising body 11, wall 12, which wall surrounds and defines an internal compartment 16. Wall 12 comprises at least one exit means 13 that connects compartment 16 with exterior of dosage form 10. Dosage form 10 can comprise more than one exit means, as presented later in the specification.

Wall 12 of dosage form 10, comprises totally, or in at least a part, a composition that is permeable to the passage of an exterior fluid present in the environment of use. Wall 12 is substantially impermeable to the passage of an antiviral drug 15, and to other optional ingredients present in compartment 16. Semipermeable wall 12 is substantially inert, that is, wall 12 maintains its physical and chemical integrity during the dispensing of an antiviral drug 16 from dosage from 10. Wall 12, in one preferred embodiment is formed totally, or in at least a part of a member selected from the group consisting of a cellulose, cellulose ether, cellulose ester and a cellulose ester-ether. The cellulose polymers comprise a degree of substitution, D.S., on the anhydroglucose unit, from greater than 0 up to 3 inclusive. By degree of substitution is meant the average number of hydroxyl groups originally present on the anhydroglucose unit comprising the cellulose polymer that are replaced by a substituting wall-forming group. Representative materials for forming wall 12 include a member selected from the group consisting of cellulose acylate, cellulose diacylate, cellulose triacylate, cellulose acetate, cellulose diacetate and cellulose triacetate. The cellulose polymers include mono, di and tricellulose, alkanylates, alkenylates, and mono, di and tricellulose aroylates. Exemplary polymers include cellulose acetate having a D.S. up to 1 and an acetyl content up to 21%; cellulose acetate having an acetyl content of 32 to 39.8%; cellulose acetate having a D.S. of 1 to 2 and an acetyl content of 21 to 35%; and, cellulose acetate having a D.S. of 2 to 3 and an acetyl content of 35 to 44.8%. More specific cellulose polymers include cellulose propionate having a D.S. of 1.8 and a propyl content of 39.2 to 45% and a hydroxyl content of 2.8 to 5.4%; cellulose acetate butyrate having a D.S. of 1.8% and an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7%; cellulose triacylates having a D.S. of 2.9 to 3% such as cellulose triacetate, cellulose trivalerate, cellulose trilaurate, cellulose tripalmitate, cellulose trisuccinate, and cellulose trioctanoate; cellulose diacylates having a D.S. of 2.2 to 2.6% such as cellulose disuccinate, cellulose dipalmitate, cellulose dioctanoate, cellulose dipentanoate; and coesters of cellulose such as cellulose acetate butyrate, cellulose acetate propionate, cellulose isopropyl acetate, and cellulose acetate pentanoate.

Additional semipermeable polymers comprise acetaldehyde dimethylcellulose acetate, cellulose acetate ethyl carbamate, cellulose acetate methyl carbonate, cellulose acetate methyl carbamate, cellulose acetate dimethyl aminoacetate; semipermeable polyamides; semipermeable polyurethanes; semipermeable sulfonated polystyrenes; semipermeable cross-linked selectively permeable polymers formed by the coprecipitation of a polyanion and a polycation as disclosed in U.S. Pat. Nos. 3,173,876; 3,276,586; 3,541,005; 3,541,006, 3,546,142; 4,950,486; 4,966,769; and 5,057,321; semipermeable polymers as disclosed by Loeb and Sourirajan in U.S. Pat. No. 3,133,132; semipermeable lightly cross-linked polystyrene derivatives; semipermeable cross-linked poly(sodium styrene sulfonate); and semipermeable cross-linked poly(vinylbenzyltrimethyl ammonium chloride). The polymers are known in U.S. Pat. Nos. 3,845,770; 3,916,899; and 4,160,020; and in the *Handbook of Common Polymers*, by Scott, J R and Roll, W J, 1971, published by CRC Press, Cleveland, Ohio.

Wall 12, in another manufacture comprises 0 weight percent to 35 weight percent of a polyethylene glycol comprising a member selected from the group consisting of a polyethylene having a 200 to 900 molecular weight a clean, thick-viscous liquid, and a polyethylene glycol having a 900 to 8,000 molecular weight a white, waxy solid. The polyethylene glycols are blended with a cellulose wall-forming polymer to increase the flexibility of wall 12, to decrease the brittleness of wall 12, and to increase aqueous fluid-flux through wall 12. The polyethylene glycol also decreases the surface tension of wall 12, thereby increasing the coating of wall 12, by increasing the wetting properties of wall 12, thereby increasing the coating of wall 12 around an osmotic core. The polyethylene glycols are compatible with dosage form 10, antiviral drug 15 and the polyethylene glycols are non-toxic. The polyethylene glycols are known in *Remington's Pharmaceutical Sciences*, 17th Ed, p 1305 (1985) published by Mack Publishing Company, Easton, Pa.

Wall 12, in another manufacture comprises 0 weight percent to 35 weight percent of a different cellulose selected from the group consisting of a hydroxypropylmethylcellulose, hydroxypropylcellulose, hydroxybutylcellulose, hydroxypropylethylcellulose, hydroxyalkylcellulose, and hydroxyethylcellulose. In the manufacture wherein wall 12 comprises more then one wall-forming component, the total weight of all components in wall 12 is equal to 100 weight percent.

Dosage form 10, as seen in opened section, depicts internal compartment 16. Compartment 16 comprises a pharmaceutically acceptable antiviral drug composition, wherein the antiviral drug is represented by dots 15. The antiviral drug 15, that can be formulated into an osmotic pharmaceutical composition for formulating dosage form 10, comprises a member selected from the group consisting of acyclovir, azidouridine, anasmycin, amantadine, bromovinyldeoxusidine, chlorovinyldeoxusidine, cytarabine, didanosine, deoxynojirmycin, dideoxycitidine, dideoxyinosine, dideoxynudeoside, desciclovir, deoxyacyclovir, edoxuidine, enviroxime, fiacitabine, foscarnet, fialuridine, fluorothymidine, fluxuridine, ganciclovir, hypericin, interferon, interleukin, isethionate, idoxuridine, nevirapine, pentamidine, ribavirin, rimantadine, stavirdine, sargramostin, suramin, trichosanthin, trifluorothymidine, tribromothymidine, trichlorothymidine, vidarabine, zidoviridine, zalcitabine, and 3-azido-3-deoxythymidine.

The antiviral drug 15 in dosage form 10 may be present as a pharmaceutically acceptable salt. The salt may be a member selected from the group consisting essentially of an inorganic, organic, hydrochloric, hydrobromic, sulfuric, nitric, phosphoric, maleic, salicylic, sulfonic, para-toluene, tartaric, citric, acetic, methanesulfonic, formic, succinic, naphthalene-2-sulfonic, isethionic, lactobionic, benzene-sulfonic, propionic, oxalic, chlorotheophylline, gluconic, and choline. The antiviral drug 15 may be present as a racemic mixture, and as their relative enantiomers, including negative optical rotation and positive optical rotation enantiomeric antiviral drugs. The dose of antiviral drug 15 in dosage form 10 is 0.05 mg to 1,200 mg, with individual dosage forms comprising 20 mg, 30 mg, 50 mg, 100 mg, 150 mg, 180 mg, 200 mg, 250 mg, 300 mg, 400 mg, 525 mg, and 750 mg of antiviral drug 15. The antiviral drugs are known in the *Pharmacological Basis of Therapeutics*, by Goodman and Gilman, 8th Ed, 1990 published by Pergamon Press.

The pharmaceutically acceptable composition in compartment 16 comprises antiviral drug 15 and a dispensing agent 17 identified by dashes. The compatible dispensing agent 17 forms a homogenous mixture with antiviral drug 15. In the composition, antiviral drug 15 and dispensing agent 17, are free of interaction and thereby dispensing agent 17 provides for the delivery of antiviral drug 15 at a controlled rate dose that is not available prior to this invention. The compatible dispensing agent 17 comprises a member selected from the group consisting of 15 wt % to 40 wt % of a polyethylene oxide having a 175,000 to 225,000 molecular weight, 15 wt % to 40 wt % of a different polyethylene oxide having a 275,000 to 325,000 molecular weight, 0 wt % to 15 wt % of a hydroxypropylmethylcellulose having a 9,000 to 35,000 molecular weight for increasing the dispensing properties of the antiviral drug composition; 0 wt % to 15 wt % of a polyvinylpyrrolidone having a 7,000 to 50,000 molecular weight for increasing the flow properties of the antiviral composition, and 0 wt % to 20 wt % of a surface-active agent selected from cationic, artionic and nonionic agent for enhancing the gastrointestinal absorption of the antiviral drug, including a cationic surface-active agent selected from the group consisting of lauryldimethylbenzylammonium halide, diisobutylphenoxyethoxydimethylbenzylammonium halide, alkyldimethylbenzylammonium halide, laurylisoquinolinium halide, cetylethyldimethylammonium halide, and stearyldimethylbenzylammonium halide; an anionic agent selected from the group consisting of alkylaryl sulphonate, capryl imidazoline, dioctylester sodium sulphosuccinic acid, sodium lauryl sulphate, potassium lauryl sulphate, sodium alkylated aryl polyether sulphate; and a nonionic agent selected from the group consisting of alkylated aryl polyether alcohol, polyethylene glycol dodecyl thioether, fatty acid amide condensate, aromatic polyglycol ether condensate, secondary amide of lauric acid, fatty acid alkanolamine condensate, sorbitan monolaurate, sorbitan monolaurate polyoxyethylene, sorbitan mono-oleate, sorbitan mono-oleate polyoxyethylene, and mannide mono-oleate.

Dosage form 10, in FIG. 3, comprises displacement layer 17. Displacement layer 17 comprises 35 wt % to 75 wt % of a polyethylene oxide identified by slant lines 18 having a 4,500,000 to 8,000,000 molecular weight; from 12 wt % to 50 weight percent of an osmotically effective solute 19 represented by a member selected from the group consisting of sodium chloride, potassium chloride, magnesium chloride, potassium sulfate, sodium sulfate, lithium sulfate, potassium acid phosphate, mannitol, urea, inositol, tartaric acid, raffinose, sucrose, glucose, sorbitol, and fructose. The osmotically effective solutes, known also as osmagents, are known in U.S. Pat. No. 4,783,337; and in U.S. Pat. No. 4,950,486. Displacement layer 17 comprises 0 wt % to 15 wt % of a hydroxypropylmethylcellulose 20 having a 9,000 to 25,000 molecular weight; 0 wt % to 15 wt % acidic carboxypolymer 21, a polymer 21 comprising acrylic acid cross-linked with a polyallyl sucrose also known as carboxypolymethylene and as carboxyvinyl polymer comprising a 125,000 to 5,000,000 molecular weight; and 0 to 5 wt % of a lubricant such as magnesium stearate, calcium stearate and stearic acid.

The phrase exit means 13 comprises means and methods through wall 12 for the metered delivery and the metered release of drug 15 from compartment 16. The exit means 13 includes at least one, or a plurality of exit means 13 as seen in drawing FIG. 4. The exit means 13 include aperture orifice, bore, pore, porous element, hallow fiber, capillary tube, porous insert and porous overlay. Exit means 13 includes a composition that erodes or is leached from wall 12 in a fluid environment of use to produce exit means in dosage form 10. Representative materials suitable for forming exit passageway 13 or a multiplicity of exit passageways 13 include erodible poly(glycolic)acid or poly(lactic acid) in wall 12, a gelatinous filament, polyvinyl alcohol, leachable materials such as fluid removable pore forming polysaccharides, salts or oxides. A passageway or a plurality of passageways can be formed by leaching a material such as sorbitol from wall 12. The passageway 13 can have any shape such as round, triangular, square, elliptical and other geometric shapes. Also, dosage form 10 can have more than one passageway in spaced apart relations, or the exit means 13 can be on a single surface or on more than one surface of dosage form 10. Exit means 13 equipment for forming exit means 13 are disclosed in U.S. Pat. Nos. 3,845,770; 3,916,899; 4,063,064; 4,088,864 and 4,950,486. Passageways formed by leaching are disclosed in U.S. Pat. Nos. 4,200,098 and 4,285,987.

The osmotic device 10 of the invention is manufactured by standard techniques. For example, in one embodiment drug 15 is mixed with the osmopolymer and pressed into a solid lamina possessing dimensions that correspond to the internal dimensions of the compartment space 16 adjacent to a passageway. In another embodiment drug 15 and other first composition 16 forming ingredients and a solvent are mixed into a solid, or a semisolid, by conventional methods such as ball-milling, calendaring, stirring or rollmilling, and then pressed into a preselected lamina forming shape. Next, a layer of a composition comprising an osmopolymer and an osmagent are placed in contact with the layer comprising the drug, and the two layers comprising the laminate are surrounded with a semipermeable wall. The lamination of the first drug composition and the second osmopolymer osmagent composition can be accomplished by using a conventional two-layer tablet press technique. The wall can be applied by molding, spraying or dipping the pressed shapes into wall forming materials. Another and presently preferred technique that can be used for applying the wall is the air suspension coating procedure. This procedure consists in suspending and tumbling the two layered core in current of air until the wall forming composition surrounds the laminate. The air suspension procedure is described in U.S. Pat. No. 2,799,241; J Am Pharm Assoc, Vol 48, pp 451–59 (1979); and, ibid, Vol 49, pp 82–84 (1960). Other standard manufacturing procedures are described in Modern Plastics Encyclopedia, Vol 46, pp 62–70 (1969); and in Pharmaceutical Science, by Remington, 14th Ed, pp 1626–1978 (1970), published by Mark Publishing Co., Easton, Pa.

Exemplary solvents suitable for manufacturing the wall, the layers include inert inorganic and organic solvents that do not adversely harm the materials and the final wall or the final laminated wall. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, chloroform, nitroethane, nitropropane, tetrachloroethane, ethyl ether, isopropyl ether, cyclohexane, cyclooctane, benzene, toluene, naphtha, 1,4-dioxane, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

DETAILED DESCRIPTION OF EXAMPLES OF THE INVENTION

The following examples are merely illustrative of the present invention and they should not be considered as limiting the scope of the invention in any way as these examples and other equivalents thereof will become apparent to those versed in the art in the light of the present disclosure, the drawings and the accompanying claims.

EXAMPLE 1

A dosage form for administering acyclovir for treating viral infected patients in need of antiviral therapy is prepared as follows: 116.25 g of polyethylene oxide having a 200,000 molecular weight is screened through a 40 mesh screen, then 116.25 g of a different polyethylene oxide having a 300,000 molecular weight is screened through a 40 mesh screen, and then 15 g of hydroxypropylmethylcellulose is screened through a 40 mesh screen and the three screened ingredients are placed into a beaker. Next, 250 g of acyclovir is added to the beaker, the ingredients mixed, transferred to a closed jar, and roll mixed for 25 minutes to effect a homogenous mix. Then, the dry mix is wetted with 275 mL of anhydrous ethanol, mixed again, passed through a 20 mesh screen and air dried to let the ethanol evaporate from the mixture. After drying, the dry mixture is screened through a 20 mesh screened to provide dry granules, to which is added 2.5 g of magnesium stearate. The final mixture is roll mixed for 5 minutes to produce a homogenous blend.

A second, push displacement composition is prepared by screening 185 g of a polyethylene oxide having a 7,500,000 molecular weight through a 40 mesh screen, then blending the screened polyethylene with 50 g of the osmagent sodium chloride. The just prepared mixture is mixed with 12.5 g of hydroxypropylmethylcellulose having a 11,200 molecular weight, and with 1.25 g of ferric oxide. The ingredients are mixed for 5 minutes, and then 300 mL of denatured, anhydrous ethanol is slowly added to the blending mixture and all the ingredients blended for an additional 5 minutes. The prepared wet mixture is passed through a 20 mesh screen and allowed to dry at room temperature for 18 hours. This dry blend is again screened through a 20 mesh screen. The screened mixture is mixed with 1.25 g of magnesium stearate.

Next, the drug composition comprising the acyclovir weighing 500 mg is added to a press and tamped, then 250 mg of the displacement composition is added to the press and tamped, and the two, separate and distinct layers are pressed under a pressure of two tons to yield an osmotic core.

Then, the osmotic core is surrounded with a semipermeable wall comprising 80 wt % cellulose acetate having an acetyl content of 39.8% and 20 wt % of aqueous flux transport polyethylene glycol having a 3350 molecular weight. The semi permeable wall forming composition is dissolved in methylene chloride:methanol, (85:15 wt:wt) solvent to make a 4% solids solution. The semi permeable wall forming composition is sprayed onto and around the bilayered, pressed core in an Aeromatic Air ® Suspension Coater. The osmotic dosage form is dried for 24 hours at room temperature. Then, two exit means 0.635 mm passageways are laser drilled through the semipermeable wall into the drug composition. Any residual solvent is removed by drying the osmotic dosage system for 40 hours at 50° C. and at a 50% relative humidity. The osmotic system is then dried at 50° C. for one hour to remove excess moisture. The dosage form exhibits a release rate of 20.175 mg/h/12 h.

EXAMPLE 2

Following the procedure of Example 1, the drug composition is prepared wherein the composition comprises an antiviral flux enhancer to increase the flux of the antiviral drug through the mucosal gastrointestinal tissue, and the antiviral flux enhancer is selected from a cationic, anionic and nonionic enhancer.

EXAMPLE 3

Following the procedure of Example 1, the drug composition is prepared comprising a member selected from the group consisting of azidouridine, didanosine, zidovudine, zalcitabine and dideoxycitidine.

EXAMPLE 4

The procedure of Example 1 is followed for manufacturing a second, displacement layer comprising 204.75 g of sodium carboxymethylcellulose, 122.5 mg of sodium chloride, 21 g of hydroxypropylmethylcellulose comprising a 9,200 molecular weight, 0.875 g of red ferric oxide and, 0.875 g of magnesium stearate.

The procedure of Example 1 and Example 4 is followed in this example to provide a displacement barrier layer, wherein the third layer comprises 20.4 mg of carrageenan, 4.5 mg of polyvinylpyrrolidone, 4.2 mg of sorbitol, 0.3 mg of potassium chloride, 0.3 mg of blue dye No. 1, and 0.3 mg of magnesium stearate. The barrier layer is positioned between the first antiviral drug layer and the second displacement layer.

EXAMPLE 5

One presently preferred embodiment of the invention pertains to a method for delivering an antiviral drug at a controlled rate and continuously to the gastrointestinal tract of a human in need of antiviral therapy, which method comprises the steps of: (A) admitting orally into the gastrointestinal tract of a human a dosage form comprising: (1) a semipermeable wall that surrounds and defines an internal compartment, said semipermeable wall permeable to the passage of fluid and impermeable to the antiviral drug, (2) an osmotic core in the compartment, said osmotic core comprising an antiviral drug layer and a displacement layer, (3) exit means in the semipermeable wall for delivering the antiviral drug from the dosage form; (B) imbibing gastrointestinal fluid through the wall into the compartment to convert the antiviral drug layer to a dispensable layer and to convert the displacement layer to an operative push layer; and (C) delivering the antiviral drug by the displacement layer expanding and thereby causing the antiviral drug to be pushed through the exit means at a controlled rate over a period of time to the gastrointestinal tract for antiviral therapy.

Inasmuch as the foregoing specification comprises preferred embodiments of the invention it is understood that variations and modifications may be made herein, in accordance with the inventive principles disclosed, without departing from the scope of the invention.

We claim:

1. A method for administering an antiviral drug to the gastrointestinal tract of a human in need of antiviral therapy, wherein the method comprises:
    (a) admitting a dosage form orally into the gastrointestinal tract of the human, said dosage form comprising:
        (1) a semipermeable wall permeable to the passage of fluid and substantially impermeable to the passage of an antiviral drug, said wall comprising a member selected from the group consisting of a cellulose acylate, cellulose diacylate, and cellulose triacylate, which wall surrounds;
        (2) a compartment comprising 0.05 ng to 200 mg of an antiviral drug and a flux promoter selected from the group consisting of a cationic, anionic, and nonionic promoter for promoting the therapeutic effects of the antiviral drug;
        (3) an exit passageway in the wall that connects the gastrointestinal tract with the compartment:
        (4) a displacement composition in the compartment:
    (b) imbibing gastrointestinal fluid through the semipermeable wall for activating the displacement composition causing the displacement composition to expand and displace the antiviral drug composition from the compartment through the exit passageway, and wherein the method is characterized by:
    (c) administering from the compartment the antiviral drug composition comprising the antiviral drug and the flux promoter to the gastrointestinal tract for antiviral therapy.

2. The method for administering the antiviral drug to the gastrointestinal tract of a human according to claim 1, wherein the antiviral drug is a member selected from the group consisting of acyclovir, azidouridine, didanosine, zidovudine, zalcitabine, and dideoxycitidine.

3. A hydro-activated osmotic dosage form for delivering a composition comprising an antiviral drug to a patient in need of antiviral therapy, wherein the dosage form comprises:
    (a) a semipermeable wall permeable to the passage of fluid and substantially impermeable to the passage of an antiviral drug, which semipermeable wall comprises a member selected from the group consisting of a cellulose acrylate, cellulose diacylate and cellulose triacylate and surrounds;

(b) a fluid-receiving internal compartment;

(c) exit means in the semipermeable wall that connects the exterior of the dosage form with the internal compartment;

(d) a fluid-activated displacement layer in the compartment for displacing the composition comprising the antiviral drug from the internal compartment; and wherein the dosage form is characterized by:

(e) a composition layer comprising 0.05 ng to 1000 mg of an antiviral drug 0 to 20 wt % of an antiviral flux promoter and means for mixing with an imbibed aqueous fluid and thereby forming a deliverable composition for delivering the antiviral drug to a patient in need of antiviral therapy.

4. The hydro-activated osmotic dosage form for delivering an antiviral drug composition according to claim 3, wherein the difficult to deliver antiviral drug is poorly soluble in an aqueous fluid.

5. The hydro-activated osmotic dosage form for delivering an antiviral drug composition according to claim 3, wherein the antiviral drug is acyclovir., 6. The hydro-activated osmotic dosage form for delivering an antiviral drug composition according to claim 3, wherein the antiviral drug is a member selected from the group consisting of azidouridine, didanosine, zidovudine, zalcitabine and dideoxycitidine.

7. The hydro-activated osmotic dosage form for delivering an antiviral drug composition according to claim 3, wherein the antiviral drug flux promoter is a member selected from the group consisting of a cationic, nonionic an anionic promoter.

8. A dosage form for delivering a composition comprising an antiviral drug to a patient in need of antiviral therapy, wherein the dosage form comprises:

(a) a wall permeable to the passage of fluid and substantially impermeable to the passage of an antiviral drug, which wall comprises a member selected from the group consisting of a cellulose acylate, cellulose diacylate and cellulose triacylate; and wherein the dosage form is characterized by comprising:

(b) a composition comprising 0.05 ng to 1000 mg of an antiviral drug and means for forming with fluid in a patient a composition deliverable by hydrofluid activity from the dosage form to the patient over time.

9. A composition comprising 0.05 ng to 1200 mg of an antiviral drug; 15 wt % to 40 wt % of a member selected from the group consisting of a polyethylene oxide having a 175,000 to 225,000 molecular weight and a polyethylene oxide having a 275,000 to 325,000 molecular weight; and 0 wt % to 20 wt % of a surface-active agent selected from the group consisting of a cationic, artionic and nonionic agent.

10. The composition comprising the antiviral drug according to claim 9 wherein the antiviral drug is a member selected from the group consisting of acyclovir, azidouridine, anasmycin, amantadine, bromovinyldeoxusidine, chlorovinyldeoxusidine, cytarbine, didanosine, deoxynojirmycin, dideoxycitidine, dideoxyinosine, dideoxvnudeoside, desciclovir, deoxyacyclovir, edoxuidine, enviroxime, fiacitabine, foscarnet, fialuridine, fluorothymidine, fluxuridine, ganciclovir, hypericin, interferon, interlenkin, isethionate, idoxuridine, nevirapine, pentamidine, ribavirin, rimantadine, stavirdine, sargramostin, suramin, trichosanthin, trifluorothymidine, tribromothymidine, trichlorothymidine, vidarabine, zidoviridine, zalcitabine, and 3-azido-3-deoxythymidine.

11. A composition comprising 0.05 ng to 1200 mg of an antiviral drug, a pharmaceutically acceptable cellulose, and a surface-active agent selected from the group consisting of a cationic, artionic and nonionic agent.

12. The composition according to claim 11, wherein the pharmaceutically acceptable cellulose is selected from the group consisting of hydroxymethylcellulose, hydroxyethylcellulose, hydroxypropylcellulose, hydroxypropylethylcellulose and hydroxypropylmethylcellulose.

13. The composition according to claim 11, wherein the antiviral drug is indicated for treating a virus infection selected from the group consisting of ovdobial herpes, cutaneous herpes, genital herpes, herpetic proctitis, varicella-zoster herpes, wart herpes, and a virus that replicates by reverse transcription.

14. A method indicated for treating a viral infection, wherein the method comprises admitting orally into the gastrointestinal tract a dosage form comprising a composition that comprises 0.05 ng to 1200 mg of an antiviral drug and a surface-active agent selected from the group consisting of a cationic, anionic, and nonionic agent, which dosage form delivers the composition at a controlled rate over a period of time to the gastrointestinal tract for antiviral therapy.

15. The method indicated for treating a viral infection according to claim 14, wherein the composition comprises a cellulose selected from the group consisting of hydroxypropylmethylcellulose, hydroxypropylcellulose, hydroxybutylcellulose, hydroxypropylethylcellulose, and hydroxyethylcellulose.

* * * * *

UNITED STATES PATENT AND TRADEMARK OFFICE
CERTIFICATE OF CORRECTION

PATENT NO. : 5,358,721
DATED : October 25, 1994
INVENTOR(S) : George V. Guittard, Patrick S.-L. Wong, Anthony L. Kuczynski, and David J. Kidney It is certified that error appears in the above-indentified patent and that said Letters Patent is hereby corrected as shown below:

Claim 1, column 10, line 37, "200 mg" should read -- 1200 mg--.

Signed and Sealed this

Seventh Day of March, 1995

Attest:

BRUCE LEHMAN

Attesting Officer    Commissioner of Patents and Trademarks